United States Patent
Boppe

[11] Patent Number: 5,819,229
[45] Date of Patent: Oct. 6, 1998

[54] SURGICAL ASSISTANCE AND MONITORING SYSTEM

[75] Inventor: Charles W. Boppe, Brookline, Mass.

[73] Assignee: Northrop Grumman Corporation, Los Angeles, Calif.

[21] Appl. No.: 553,166

[22] Filed: Nov. 7, 1995

[51] Int. Cl.⁶ .................................................. G06F 17/40
[52] U.S. Cl. ............................ 705/2; 364/400; 600/301; 705/3; 707/104
[58] Field of Search ..................................... 395/202, 203; 128/920, 630, 653.1, 653.2, 897, 898; 606/130; 705/2, 3; 600/300, 301, 407, 411, 427; 364/400; 707/104

[56] References Cited

U.S. PATENT DOCUMENTS

| | | | |
|---|---|---|---|
| 4,489,387 | 12/1984 | Lamb et al. | 128/630 |
| 4,965,879 | 10/1990 | Fischer, Jr. | 364/424 |
| 5,111,402 | 5/1992 | Brooks et al. | 364/424 |
| 5,146,439 | 9/1992 | Jachmann et al. | 369/25 |
| 5,189,606 | 2/1993 | Burns et al. | 364/401 |
| 5,270,920 | 12/1993 | Pearse et al. | 364/401 |
| 5,270,945 | 12/1993 | Heath et al. | 364/497 |
| 5,441,047 | 8/1995 | David et al. | 600/301 X |
| 5,544,649 | 8/1996 | David et al. | 600/301 |
| 5,579,378 | 11/1996 | Arlinghaus, Jr. | 128/904 X |
| 5,647,361 | 7/1997 | Damadian | 128/683.2 |

*Primary Examiner*—Edward R. Cosimano
*Attorney, Agent, or Firm*—Terry J. Anderson; Karl J. Hoch, Jr.

[57] ABSTRACT

An integration of a plurality of subsystems of various types of equipment into a single monitorable system or unit, and more specifically a surgical assistance and monitoring subsystem integrating arrangement which enables the enhancement of the functionality and capabilities of the integrated system. A connection of each respective surgical assistance and monitoring-system to a common network providing for a database management center enables the establishment of a unified statistical basis for surgical team feedback and provides information regarding a particular patient's surgical procedure and characteristics and past medical history, which can be employed and correlated over wide geographical areas by logging in the database for informative purposes by various surgical teams experiencing similar problems and implementing identical functions on other patients.

4 Claims, 7 Drawing Sheets

Typical Operating Room Equipment

| Equipment | Manufacturer | Functions | Systems |
|---|---|---|---|
| Anesthesia Machine | Hewlett-Packard<br>Ohmeda | Ventilator<br>(Supplies Oxy And Gas Under Pressure At Specified Rate)<br>Measurement<br>(Blood Gas Levels,<br>Body Core Temp)<br>Control<br>Data Display | Sensors<br>Electrical<br>Pneumatic<br>Mechanical<br>Displays |
| Heart Monitor System | Hewlett-Packard<br>Siemens<br>Datascope | Measurement<br>(Heart Elect. Pattern,<br>Multiple Blood Pressures)<br>Data Display<br>Control<br>Defibrillator Coord.<br>Defib. Chrg/Dischrg | Sensors<br>Electrical<br>Pneumatic<br>Mechanical<br>Displays |
| Heart-Lung Machine | TBD | Ventilator<br>(Supplies Oxy Under Pressure At Specified Rate)<br>Measurement<br>(Blood Gas Levels, Body Core Temp)<br>Control<br>Blood Pumping<br>Data Display | Sensors<br>Electrical<br>Pneumatic<br>Mechanical<br>Liquid<br>Displays |

FIG.2A

| Equipment | Manufacturer | Functions | Systems |
|---|---|---|---|
| Op. Room Table | Ansco | Patient Support (Re-Arrangeable) Control | Electrical Mechanical |
| Hypothermia Blankets | American Hamilton | Measurement (Temperature Levels) Data Display Control | Sensors Electrical Liquid Thermal Mechanical Displays |
| Blood Warmer | Feswell | Measurement (Blood Temp) Control Data Display | Sensors Electrical Liquid Thermal Mechanical Displays |
| Sterilizer | Ansco | Sterilization (Autoclave Steam Pressure Or Gas) Control | Electrical Mechanical Pneumatic Thermal Sensors |

FIG.2B

| Equipment | Manufacturer | Functions | Systems |
|---|---|---|---|
| Endoscopy System | Olympus<br>Cauftron<br>Trimiton | Laser Incision<br>Optical Display<br>For Above<br>(Photo/Video) | Optics<br>Electrical<br>Laser<br>Displays |
| Emulsifier/Cauterizer | Phago | Dissolves Mass<br>Infection Preven.<br>Control | Electrical<br>Liquid<br>Thermal<br>Mechanical<br>Chemical |
| Lithotripsy System | Zeiz | Micro-Surgery | Electrical<br>Liquid<br>Chemical<br>Sensors |
| Smoke Filtration<br>System | Stackhouse | Air Filtering<br>(Laser Surgery<br>Environment) | Electrical<br>Mechanical |

FIG. 2C

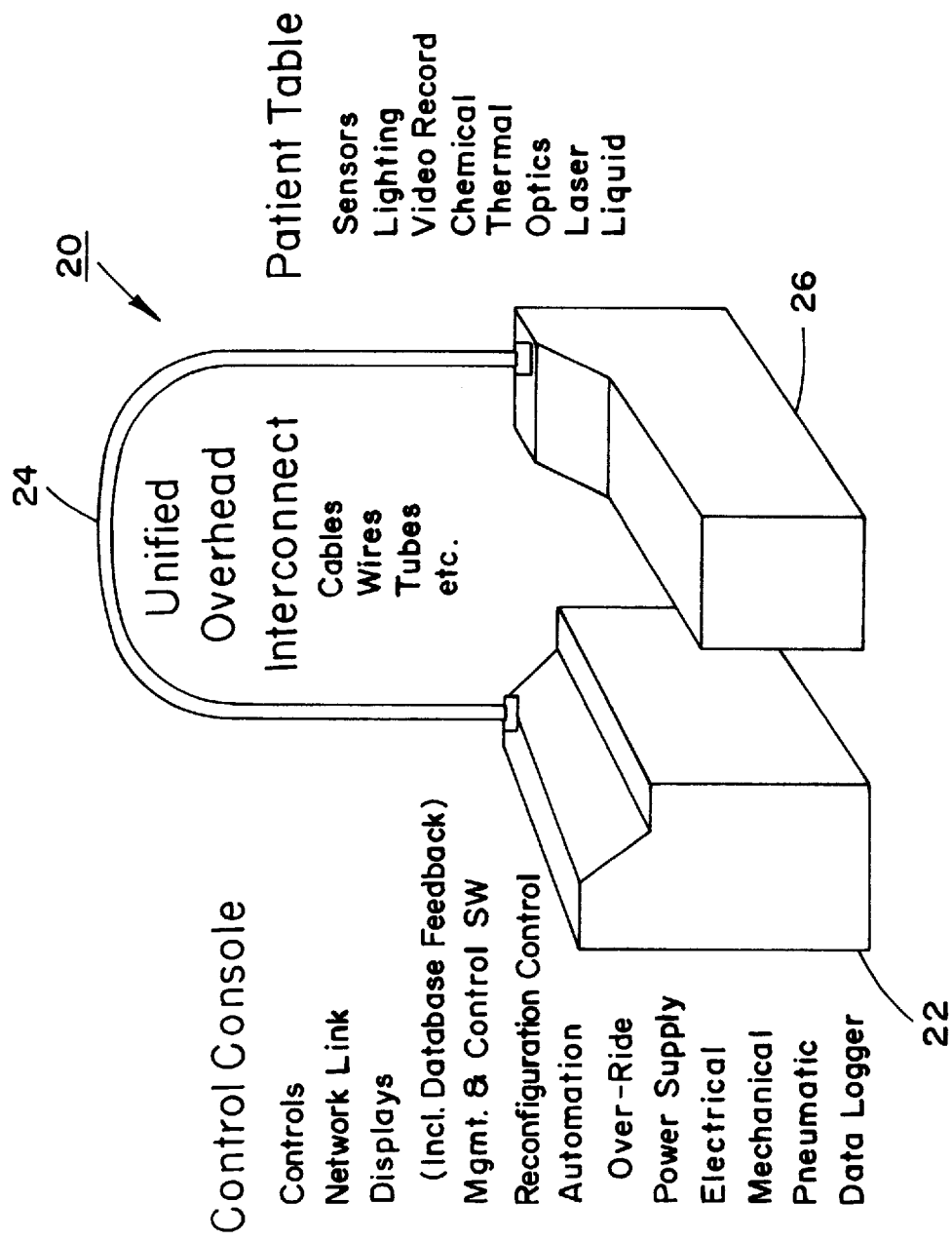

SURGICAL ASSISTANCE AND MONITORING SYSTEM

BACKGROUND OF THE INVENTION

1. Field of the Invention

The present invention relates, in general, to the integration of a plurality of subsystems of various types of equipment into a single monitorable system or unit, and more specifically pertains to a surgical assistance and monitoring subsystem integrating arrangement which enables the enhancement of the functionality and capabilities of the integrated system.

The integration of existing subsystems into a single monitorable system or primary unit through the intermediary of integrating subsystems; such as, for instance, electrical, mechanical, hydraulic, pneumatic, chemical and optical subsystems, has become of extreme importance in attempting to control the ever burdening and drastically increasing costs of constantly more complex technological devices through the elimination of entire essentially duplicate subsystems. In particular, the integration of various cross-subsystems possessed of a commonality of other component elements; for example, such as controls, pumps, motors, solenoids, relays, switches, displays, fasteners, valves and other basic components, results in further savings and simplification through the elimination or reduction of such subsystem duplications.

In essence, the integration of subsystems and consequent reduction in duplications thereof is considered to be of particularly important significance with regard to surgical and medical procedures, wherein the vast majority of hospital and clinical operating rooms are presently equipped with ordinarily well over a dozen different types of machines and systems which are utilized to support surgical procedures. Among these various subsystems, installation, operating and maintenance costs are generally calibrated with respect to the aspects of the presence of a multiplicity of manufacturers and diverse service organizational environments, the significant variations and locally imposed equipment standards and capabilities which are widely divergent over various geographical locations, not to mention the lack of any systematic process coordination for archiving procedural events and outcomes, and the various aspects of the insurance and legal systems which function to consider liabilities on the basis of the diversities in subsystems currently being employed.

At this time, health care expenditures in the United States are projected to grow from approximately 10% of the gross domestic product to approximately 20% thereof, potentially imposing considerable financial burdens on the taxpayers in sustaining such health care expenditures. Accordingly, future government influences over projected expenditures of the health care industry may readily include the concept that pressures will be exerted to attempt to reduce financial costs, possibly through the provision of standardized services, and to minimize legal liability issues which may arise from potential problems encountered due to the diverse and essentially non-standardized surgical equipment and procedures currently employed by health care professionals in different geographical areas.

Among costs which are related to surgical and hospital expenses, consideration must be given to the fact that approximately 43% of currently encountered disbursements are related to surgery, approximately 42% to pre- and post-operative medical care and patient recovery, and approximately 15% to diagnostic and testing procedures. All of these aspects, as discussed in the *American Journal of Public Health,* March 1993 issue, Pages 347–355, and particularly those related to surgical procedures and operating room equipment, necessitate the utilization and provision of complex, expensive and frequently unnecessarily duplicated subsystems.

Thus, by integrating the subsystems into a single unit or monitorable system, lower costs can be expected in the reduction or even elimination of equipment and/or procedural duplications, and whereby a portion of any such savings can be readily applied to obtaining higher levels of protection against equipment failure via controlled redundancy, and redundancy maintenance and repairs can be accomplished by a single provider who is fully conversant with the technological aspects of the resultant monitorable integrated system or single unit.

The foregoing further lends itself to the further advantage that, in conjunction with subsystem integration into a single and more compact system or unit; with such integration, for example, being embodied in a surgical or surgeons' assistance and monitoring (SAM) concept, may be employed in connection with a regional or even global database management, whereby this may lead to an advanced standardization over considerable and extensive geographic regions. This, in effect, may result in an improved overall surgical team and system performance and enhanced productivity at lower costs with attendant potential reductions in health insurance and legal costs.

For example, the database may be utilized in conjunction with the integrated surgical assistance and monitoring (SAM) unit, which provides for reduced equipment costs and the elimination of duplicate subsystems, reduced maintenance and repair costs and possible utilization of a single equipment supplier or at least fewer suppliers than at present, reconfiguration for enhanced failure protection, improved functionality and automation, reduced equipment size and potential physical entanglement due to subsidiary operating room structure and elements, and a potential for future upgrades in the equipment at relatively moderate expenditures. The integrated SAM database which is contemplated to provide for geographical correlation between any number of surgical or operating facilities on either a national or even on a world-wide or international basis, may provide for unified procedural recording for an outcome analysis of the surgical team experience through base feedback, operating room activities, advanced standardization and teachings regarding various surgical techniques employed in the correlation of the condition of the patient, the actions of the surgical team, and the subsystems performance response.

2. Discussion of the Prior Art

The concept of employing subsystem integration into a single unit or total system and resultant monitorable correlation of the functions and outputs of the various subsystems are currently well known in the aircraft industry, wherein the integration of various subsystems permits for higher levels of functionality and support over the control of the aircraft. In a somewhat analogous manner, surgical operating teams within the U.S. health care industry currently perform operating procedures employing a considerable number of different supporting machines and systems, frequently numbering more than a dozen such diverse systems in an operating room. Individual members of the surgical team; for example, such as the surgeon, neurosurgeon, anaesthesiologist, and so forth, traditionally exert complete control over their specific equipment acquisitions, and this control is implemented independently or autonomously of other operating or surgical team members. The operating room or surgical equipment suppliers generally function within this particular environment and, as a result, a considerable number of diverse organizations and manufacturers build, maintain and repair their respective surgical devices and equipment systems. The large number of currently employed individualized operating room devices result in a duplication of required surgical subsystems; for instance, such as those of an electrical, mechanical, optical, chemical, pneumatic, thermal or hydraulic nature. The foregoing also applies to the multiple and complex controls and monitoring displays normally employed in the operating room. Inasmuch as the suppliers of these surgical devices or systems are essentially uncoordinated or, in effect, provide the hospitals or surgeons independently, the different part types and components within each of the independent subsystems are considerable in their variations and excessive in number, with the result that these features unnecessarily increase the cost of such equipment. Moreover, when maintenance and repairs are required, there is of necessity encountered an involvement of a considerable number of different organizations and manufacturers, each with their own associated overhead expenses and apparent lack of standardization, thereby increasing the life-cycle cost of the equipment.

Moreover, upon occasion, during the implementation of surgical procedures, the largely independent functionality of surgical team members and their specific types of equipment renders it difficult. to identify and remedy particular and potentially life-threatening problems which may have been encountered in view of the large number of existent potential variables and complexities of the specific situations.

When unexpected situations develop during the implementation of surgical procedures, the operating team must determine a course of action, and whereby the resulting real-time decision process is predicated on the experiences and training of each of the surgical team members. The final approach selected in attempting to solve the problem which may be in the nature of a life-threatening situation to the patient being operated on, would be different from that which would be encountered if the surgical team had several weeks to do research and to be able to consult each other and other experts on the matter. The resulting real-time decision environment is constrained and impaired but is the most which can be expected with the diverse subsystems currently employed in contingencies of this nature.

The inherent independence of each of the surgical team members and, on a larger scale, the independence of surgical teams in hospitals from one geographical region to another, results in a broad spectrum in the diversity of applied standards and capabilities. Hereby, the explosive growth of the various and independently supplied medical and surgical devices and systems in the operating room has resulted in the presence of a labyrinth of interconnecting wires, tubes and cables for the systems or devices which collectively may exert an adverse effect on the overall performance of the surgical team, whereby efficiency and, potentially most importantly, the safety of the patient may be compromised.

Currently, many subsystems in various fields of technology are adapted to be combinable into units or systems to provide redundancy and failure protection, reconfiguration and other protective features which are intended to safeguard the user and the equipment, while also reducing costs by an appreciable extent.

Thus, Heath et al. U.S. Pat. No. 5,270,945 discloses a process environment monitoring system which collects and tests air samples from a number of different sample locations. The entire system is adapted to integrate a plurality of subsystems each adapted to provide information concerning a specified function wherein a data processing unit services a number of tasks to make the process environment monitor a fully integrated system.

Fischer, Jr. U.S. Pat. No. 4,965,879 describes a system for integrating subsystems in an aircraft, wherein the entire vehicle management system (VMS) is completely computer-based and adapted to centralize the computation of functions utilized by several subsystems, integrating the control of the flight control functions, the compressor control, the rotor conversion control, vibration alleviation by higher harmonic control, engine power anticipation and self-test. All of these data are collected in a single flight control computer and wherein the vehicle management system utilizes equivalent redundancy techniques to attain quadruple equivalency levels, including alternate modes of operation and recovery means to back up any functions which fail and also employs back-up control software for software redundancy.

Brooks et al. U.S. Pat. No. 5,111,402 discloses an integrated aircraft test system which will functionally test the components of subsystems of the aircraft during its manufacture and subsequent maintenance. The system incorporates a plurality of automated test equipment carts, each of which in turn contains a number of processor-controlled instruments for performing functional tests on specific components or subsystems which comprise a specific aircraft system. The remote access terminal is connectable to a central control unit in order to enable personnel to receive instructions for manual tests and including means for entering test results into the system. Hereby, the central control system reviews the results of the functional tests performed in the aircraft and broadcasts appropriate messages if functional tests were missed or failed, or if the aircraft passed its functional testing.

Burns et al. U.S. Pat. No. 5,189,606 discloses an integrated construction cost generator system utilized to develop costs for construction projects so as to analyze and estimate facilities associated with major weapon programs, for administrative medical and support facilities, as well as for runways and taxiways for aircraft, and for developing the life-cycle course for various construction projects. Hereby, this system is adapted to integrate the information received for various subsystems relative to the facilities as well as the quantities of each product required to complete each building type and estimating tools include direct course, life-cycle course and modifiers. Any direct course is then further broken down into generic models, comparative systems and a quantity take-off system to provide an accurate read-out as to cost estimates in comparison with conventional techniques.

Jachmann et al. U.S. Pat. No. 5,146,439 discloses a records management system including dictation and transcription capability wherein the integrated system is utilized for the prompt and efficient management of a patient's medical records. The system incorporates digital dictation subsystems with a number of dictation input units and a number of transcription output units whereby the final format provides a complete document presenting a report, selected portion of that report being extractable to form a summary report by the system database manager.

Pearse et al. U.S. Pat. No. 5,270,920 discloses an expert system scheduler and scheduling method which is utilized with training systems, and wherein it includes a computer network having terminals located at a central site, and a plurality of training sites at other remote sides. The computer database is located at a central site and the training facilities are located at training sites whereby computer terminals are connected together in a computer network by both dedicated and dial-up telephone lines. The schedule employed in the system comprises an integrated system of hardware and software which is integrated into the already existing training system and provides for centralized information.

SUMMARY OF THE INVENTION

Accordingly, it is an object of the present invention to provide a single unit or monitorable system which is obtained through the integration of the autonomous subsystems of current equipment units which are employed for surgical assistance and monitoring purposes. Hereby, component or subsystem duplication and redundancy can be readily eliminated, and a portion of the financial savings applied to higher levels of controlled redundancy or failure protection by reconfiguration, and whereby any required maintenance and repairs of equipment can be accomplished by a single equipment provider.

Integration of the subsystems will permit higher levels of functionality in support of a surgical team, facilitate lower power consumption and economy of scale for unified subsystem components, and automating various tasks now manually performed so as to free up a surgical team for more direct patient observation time.

Another aspect provided for by the integrated system pursuant to the invention resides in a unified overhead connect which will reduce the hazards for a surgical team due to the installation of fewer cables, tubes, wires, stands and carts normally employed in operating rooms, thereby improving efficiency and reducing potential accidents to personnel.

Another feature resides in integrating the various components of electrical, chemical, hydraulic and mechanical devices into a single unit, and also providing cross-subsystem commonality for the remaining components, such as pumps, motors, solenoids, relay switches, and the like.

Pursuant to the invention, it is also possible to provide for an overall parameter data logger which will in time-sequence record each procedure implemented and when coupled with a so-called "big picture" and close up detailed video, provide for an accurate record of the patient characteristics and team actions and decisions for future assessments and database upgrades, such as for teaching, liability resolution and database management system real-time feedback standardization.

A connection of each respective surgical assistance and monitoring system to a common network providing for a database management center enables the establishment of a unified statistical basis for surgical team feedback and provides information regarding a particular patient's surgical procedure and characteristics and past medical history, which can be employed and correlated over wide geographical areas by logging in the database for informative purposes by various surgical teams experiencing similar problems and implementing identical functions on other patients.

BRIEF DESCRIPTION OF THE DRAWINGS

Reference may now be had to the following detailed description of a preferred embodiment of the invention taken in conjunction with the accompanying drawings; in which:

FIGS. 2A through 2C illustrate a tabulation of typical operating room equipment provided for in major hospital operating rooms;

FIG. 3 diagrammatically illustrates a surgical assistance and monitoring unit for the integration of operating room subsystems pursuant to the present invention;

DETAILED DESCRIPTION OF PREFERRED EMBODIMENTS

In numerous and diverse fields of industrial, research and medical applications, the ever-increasing demands on technology have created a multiplicity of subsystems, particularly the sophisticated equipment utilized in operating rooms of hospitals and clinics, thereby leading to frequently untenable levels of financial expenditures in the procuring and maintaining of equipment and various subsystems, while also lacking in the provision of any sort of standardization among the various types of components employed throughout widely dispersed national and international geographical regions.

Figure 1:
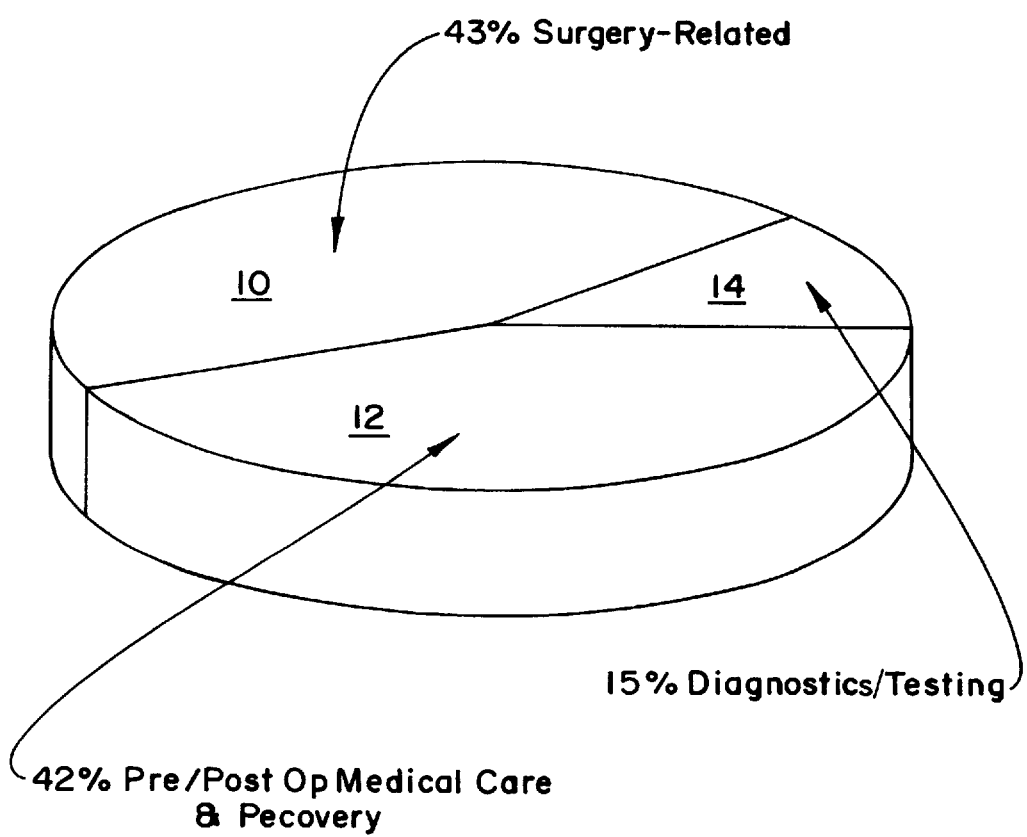
FIG. 1 illustrates a pie chart of commonly encountered surgical and hospital cost distributions in the treatment of a typical patient.

In particular, referring to the United States health care system, as illustrated in the pie chart of FIG. 1, surgical and hospital costs for a typical patient are roughly divided into three major portions, wherein area 10 indicates that disbursements or costs are approximately 43% related to surgery; area 12 approximately 42% to pre- and post-operative medical care and recovery, including hospital and nursing costs; and area 14 the remaining 15% devoted to diagnostics and testing of the patient.

Currently, the use of medical devices or equipment is increasing at a rate of nearly 10% each year on a world-wide basis, and in accordance with investigations, health care and its related expenditure is perceived as the technology which will affect patients or prospective patients most extensively over the next ten years.

The dramatically rising costs of health care, both in the United States and on a world-wide basis, has caused the various national governments to identify a number of requirements which will impact future medical industry investments; such as:

Pooling of Resources

Networking

Methodical Analysis

Reduced Liability Redundancy

Safety and Efficiency Improvements.

Among the most significant aspects of the foregoing there resides the fact that in the past, and even at the present time, in the implementation of a surgical procedure, each member of the surgical team; for example, a neurosurgeon, general surgeon, anaesthesiologist, and so forth, has been able to procure the particular type of operating room equipment as desired by that participant. This has lead to a diversity of types of equipment generally employed for the same purpose, which all but prohibits any standardization and the constraining of costs.

For example, as illustrated in FIGS. 2A through 2C, there is set forth a tabulation of typical operating room equipment including a listing of major manufacturers, functions and systems, from which it can be noted that the operating rooms are usually equipped with well over a dozen major operating room equipment units, devices or subsystems. The lack of any standardization inhibits their integration or reduction into tenable numbers which would render the entire procurement thereof cost-effective, particularly in comparison with the large and uncontrolled types of devices currently being procured by different operating surgical personnel from a multiplicity of vendors or manufacturers. In order to reduce costs in the procurement of health care equipment, and particularly operating room systems which consist of a considerable number of highly complex and expensive surgical subsystems, through the integration of; for example, existing electrical, mechanical, hydraulic, pneumatic, chemical and optical subsystems among others into a single unit or monitorable system, there can be achieved considerable savings in original equipment, replacement and maintenance costs based on the elimination of entire duplicate systems. Moreover, cross subsystem commonalities of various component elements, such as controls, pumps, motors, solenoids, relays, switches, displays, fasteners, valves and other elements, may readily result in further extensive savings. The standardization of the overall components in a single unit or system which results in a high level of hardware integration serves to impart flexibility and adaptability; in effect, as the operating experience of the system accrues, the functionality and capabilities of the system or unit can be enhanced by means of upgrades, such as through control and management software rather than supplying expensive hardware upgrades and connections.

Thus, as is shown in FIG. 3 of the drawings, representing generally diagrammatically a surgical assistance and monitoring unit 20 pursuant to the invention, one major portion of the integrated unit or system comprises a control console 22 incorporating a plurality of elements such as controls, network links, displays including possible database feedback, management control software, reconfiguration control, automation override, power supply, electrical and mechanical devices and a pneumatic data logger.

Connected to the control console 22 by means of unified overhead extending interconnecting cables, wires, conduits 24 and the like, which are consequently placed out of the way of operating room personnel is a patient table 26 which, as is known in the technology, may incorporate suitable sensors, lighting, video records, chemical, thermal, optical, optics, laser and liquid supply components.

The integration of these particular features aspects into a single control console 22 and, respectively, a patient table 26 which are operationally interconnected by unified overhead extending connecting structure 24, not only simplifies the entire integrated system which may be potentially housed in only one or two receptacles, but also enables standardization of such components which may be adapted to different surgical procedures and surgeons of various types of disciplines without any unnecessary redundancy or duplication of equipment.

Figure 4:
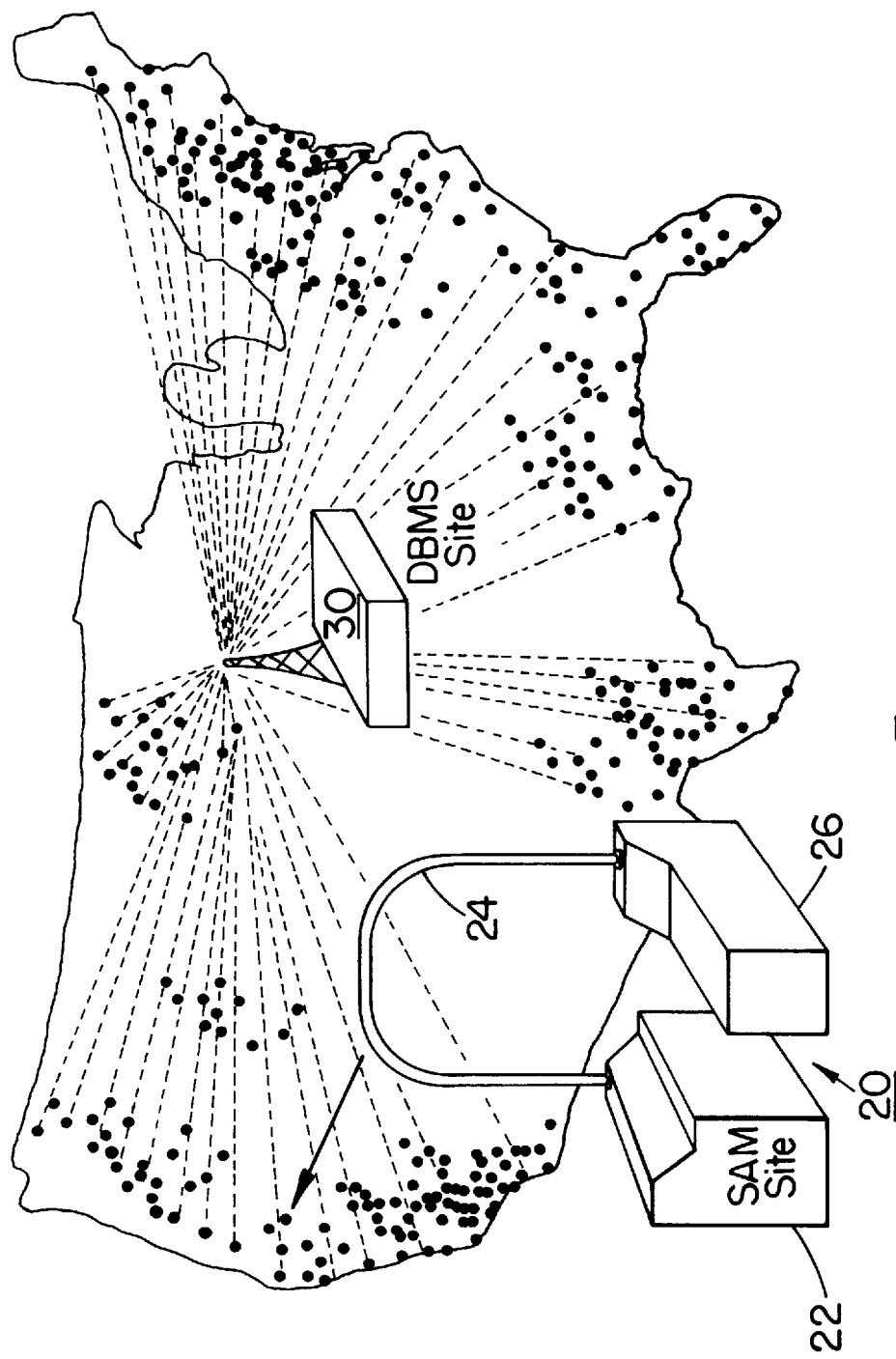
FIG. 4 graphically illustrates a typical interfacing between a plurality of surgical assistance and monitoring units located geographically dispersed throughout the United States and a database monitoring or management site.

As is indicated in FIG. 4 of the drawings, on a national basis illustrating a map of the United States, although other geographical regions may be contemplated by the present invention, either more localized,—such as state-wide or the like, or conversely on international or world-wide scale, the surgical assistance and monitoring unit 20 as described with regard to FIG. 3, may be linked to a central database monitoring source 30, wherein each black dot represents a specific or individual location of a surgical assistance and monitoring unit 20.

The surgical assistance and monitoring units 20 are connected in a network to a common database management system (DBMS) 30 so as to enable the establishment of a unified statistical basis for surgical team feedback to a single source which may be readily tapped or electronically consulted by various surgical teams at any geographical location of a surgical assistance and monitoring unit 20 which is connected to the database management system 30. This facilitates the provision of the real-time action and response capability which is a function of a particular patient's surgical procedure characteristics and past medical history. This centralized database management system 30 enables the surgical team to draw upon the experiences of many other surgical teams who have been exposed to similar experiences with other patients, and may enable them to quickly implement corrective or correlative action during surgery which, in many instances, may save a patient's life.

Figure 5:
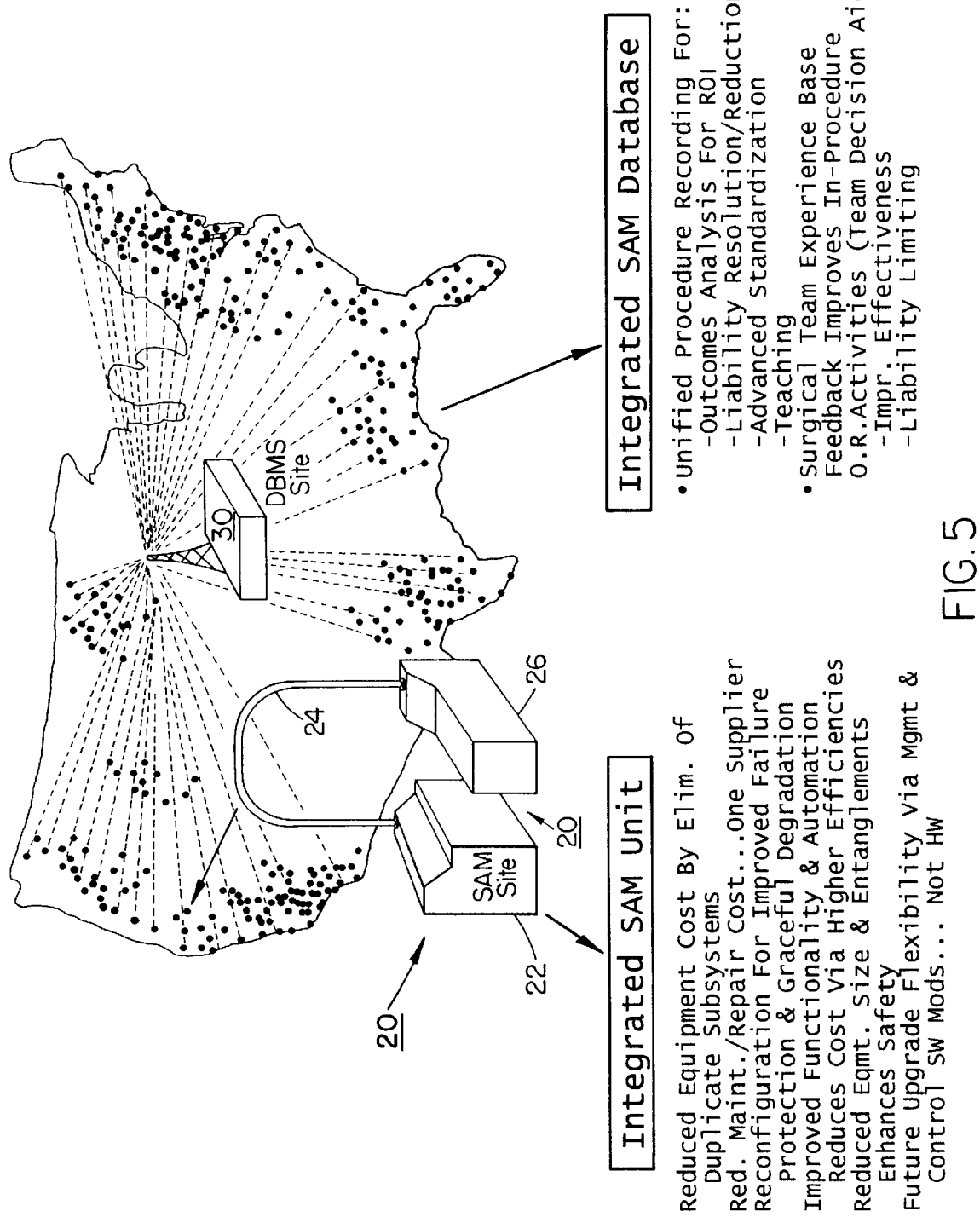
FIG. 5 illustrates a detailed view of the arrangement of FIG. 4 tabulating the particular features derived by the interfacing.

As is illustrated in FIG. 5 of the drawings, the benefits which are derived by the integration of the surgical assistance and monitoring (SAM) unit 20 with an integrated database monitoring system (DBMS) 30 connected thereto through a centralized database permits the integrated SAM unit to reduce equipment costs through the elimination of duplicate subsystems;

reduce maintenance and repair costs through the possible provision of one or only two suppliers for each completely integrated system containing a multiplicity of subsystems;

reconfigure the system for improved failure protection and permissible degradation;

provide an improved functionality and automation which will reduce costs due to the higher efficiencies obtained;

reduce equipment size due to the integration of the subsystems and any entanglements by personnel because of the use of the overhead connection of the control console to the patient table, thereby increasing the degree of safety to the operating personnel; and enable future equipment upgrade flexibility through management and control software modulation without revision of the hardware.

On the other hand, the utilization of the integrated database monitoring system connected to the surgical and assistant monitor units throughout the geographical areas enables a unified procedure in recording outcome analysis;

liability resolution and reduction;

advanced standardization, provides for teaching due to the standardized approach enabled thereby;

provides a basis for surgical team experience monitoring and data archiving;

feedback received from the various SAM units improves in-procedure operating room activities; assists in the decisions by the operating team during the surgical procedure;

improves the effectiveness and concurrently due to its capability of providing instant information regarding the latest surgical techniques on a geographical basis, which may be local, national or world-wide; and reduces any potential legal liabilities by indicating the surgical team has utilized all of the experience and data derived through the database.

The foregoing enables the realization of a vast standardization of equipment and reduced acquisition costs, enabling the use of only a single or limited number of suppliers and maintenance and repair providers;

enables operating cycle time reduction due to increased automation; and integrated design permits functional reconfiguration after equipment failures and advanced standardization of equipment on a geographically broad basis.

From the foregoing, it becomes readily apparent that the invention is adapted to provide a unique integration of various subsystems which not only are not limited to medical and surgical applications, but may also find widespread practical applications in commercial and legal areas, in manufacturing plants, in the procurement of military hardware and equipment and standardization of various military subsystems, and with regard to information required by law firms, which may be of legal significance over widespread geographical areas.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. An integrated surgical assistance and monitoring system for functionally and structurally integrating a plurality of surgical subsystems including operatively integrated surgical devices so as to form a unitary arrangement of a generally standardized nature, said subsystems comprising individualized components each having a specified operative function; means operatively interconnecting said subsystems so as to combine the functions thereof into a monitorable unit of a non-redundant and compact integrated system, said subsystems comprising a control console operatively interconnecting said surgical devices, and a patient table, said subsystem components including selectively operating electrical, mechanical, hydraulic, pneumatic, chemical and optical subsystems operatively combined with said control console and said patient table, and interconnecting means for functionally interconnecting said control console and said patient table database management means being operatively linked with said system for retrieving and archiving data from said system, and at least one other integrated assistance and monitoring system being linked to said database management means for retrieving and transmitting data thereto and for exchanging information with said first-mentioned integrated assistance and monitoring system.

2. An integrated assistance and monitoring system as claimed in claim 1, wherein said means for functionally interconnecting said control console and said patient table comprises a unified overhead connecting structure selectively incorporating electrical cables, wires and supply conduits.

3. An integrated assistance and monitoring system as claimed in claim 1, comprising a plurality of said systems being operatively interfaced with a centralized located one of said database management means.

4. An integrated assistance and monitoring system as claimed in claim 3, wherein said database management means facilitates recording of data received from said plurality of assistance and monitoring systems and providing feedback of data to respective of said systems in response to retrieval of data from said respective interfaced systems.

* * * * *